US00PP08317P

United States Patent [19]

Vletter

[11] Patent Number: Plant 8,317

[45] Date of Patent: Jul. 20, 1993

[54] LILY PLANT NAMED PESARO

[75] Inventor: Floris Vletter, Rijnsburg, Netherlands

[73] Assignee: Gebr. Vletter & J.A., Rijnsburg, Netherlands

[21] Appl. No.: 796,691

[22] Filed: Nov. 21, 1991

[51] Int. Cl.[5] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A new lily plant named Pesaro, characterized by its very large flowers, very tall plant height, vigorous growth habit, pink flower color with many darker red-pink spots and white near base, strongly curved petals, and its contrasting orange pollen.

1 Drawing Sheet

The present invention comprises a new and distinct cultiver of lily, botanically known as Lilium, commercially known as Lilium oriental hybrid, and hereinafter referred to by the cultivar name Pesaro. The parents were oriental varieties belonging to division VII(b) described in "Classification of Lily Cultivars into Divisions" published by Victoria Mathews, The Royal Botanic Gardens, Kew (1989).

The new cultivar is a product of a planned breeding program which had the primary objective of creating new lily cultivars with distinctive pink color, long firm stems, and good forcing characteristics.

The new cultivar was originated from a hybridization made by the inventor in a controlled breeding program in Rijnsburg, The Netherlands in 1981. Both the male and female parents were unnamed seedlings.

The new cultivar was discovered and selected as one flowering plant within the progeny of the stated cross by the inventor in July 1981 in a controlled environment in Rijnsburg, The Netherlands.

The first act of asexual reproduction of the new cultivar was accomplished by the inventor when scales were taken from the initial selection in 1985 in a controlled environment in Rijnsburg, The Netherlands.

Horticultural examination of selected units has demonstrated that the combination of characteristics as herein disclosed for Pesaro are firmly fixed and are retained through successive generations of asexual reproduction.

The new cultivar has not been observed under all possible environmental conditions. The phenotype may vary significantly with variations in environment such as temperature, light intensity, and day length, without, however, any variation in genotype. The following observations, measurements and comparisons describe plants grown in Wageningen and Rijnsburg, The Netherlands under greenhouse conditions which approximate those generally used in commercial practice.

The following traits have been repeatedly observed and are determined to be basic characteristics of the new cultivar which in combination distinguish this lily as a new and distinct cultivar.

1. Very large flowers;
2. Pink flower color with many dark red-purple spots or markings, and white near base;
3. Strongly curved petals;
4. Orange pollen pleasantly contrasts with flower color.

Of the many commercial cultivars known to the present inventor, the most similar in comparison to the new cultivar is Stargazer. In comparison to Stargazer, Pesaro has longer stems and a more intense pink flower color. When flowering is forced under natural light, Pesaro produces an inflorescence approximately 6 days earlier than Stargazer, under the same growing conditions. Pesaro is fertile.

The accompanying photographic drawing shows typical flower characteristics of the new cultivar, with colors being as true as possible with illustrations of this type. The photograph comprises a top perspective view several flowers open and buds at various stages.

In the following description, color references are made to The Royal Horticultural Society (R.H.S.) Color Chart. The color values were determined at Wageningen in 1988–1989 and Rijnsburg in July 1991.

Origin: Seedling from Breeding Program.

Parentage:

*Seed parent.*—Unnamed seedling.

*Pollen parent.*—Unnamed seedling.

Classification:

*Botanical.*—Lilium.

*Commercial.*—Oriental hybrid.

THE PLANT

Form: A single stem carrying numerous pedicels alternately arranged.

Height: Very tall; 130 cm at time of opening of anthers of first flower.

Growth habit: Vigorous.

Stem: Color 187B; circular in transverse section; internodal length 2 cm and uniform; anthocyanin pigmentation present.

Foliage:

*Quantity.*—55–65 leaves depending on growing conditions.

*Size of leaf.*—Mature leaves are medium in length (14 cm), and medium to wide in width (4 cm).

*Shape of leaves.*—Elliptical, reflexing at tip; edges are strongly turned.

*Texture.*—Smooth with weak glossiness; no pubescence on lower side.

*Color.*—Medium green 137A.

Bulbs:

*Size.*—Outlet 6–30 cm.

*Color.*—Purplish brown.

Roots: Both stem and contractile present.

THE BUD

Form: Tapering (like a lancet).

Size: 10 cm prior to opening.

Opening: Unfolds normally.

Color: 55B.

Tepals: Folded, three visible.

THE FLOWER

Blooming habit: Raceme.

Size: Large; 21 cm in total diameter, depending on growing conditions.

Borne: Horizontal.

Shape: Generally in form of hexagonal star; bowl-shaped in cross section.

Tepalage:

*Number of tepals.*—Six.

*Arrangement.*—Three inner and three outer each with marginal undulation.

*Color.*—Upper surface: Light purple 65B middle and 65D base and tips. Lower surface: Light purple 65C.

*Spotting or marking.*—Dark pink red spots, the diameter of each of which is 0.5–2.5 mm.

Nectaries and papillae: Present; very strong.

Pedicel:

*Length.*—9 cm (of first flower).

*Color.*—Dark reddish brown.

*Form.*—Strongly curved.

Texture: Papillose.

Disease resistance: No disease problems noted to date.

Fragrance: Present; weak.

Lasting quality: Excellent.

REPRODUCTIVE ORGANS

Stamens, anthers:

*Arrangement.*—Anthers form a generally circular pattern.

*Length.*—Short to medium, 6.5 cm.

*Number.*—Six.

*Filaments.*—Green.

Pollen color: Dark brown to dark orange brown.

Anther color: Purple.

Pistils: Green style; total length of pistil 9.5 cm.

Stigma: Triangular in shape; purple stigma.

Ovaries: Triangular in shape; other characteristics typical of oriental lily varieties.

I claim:

1. A new and distinct lily plant named Pesaro, as

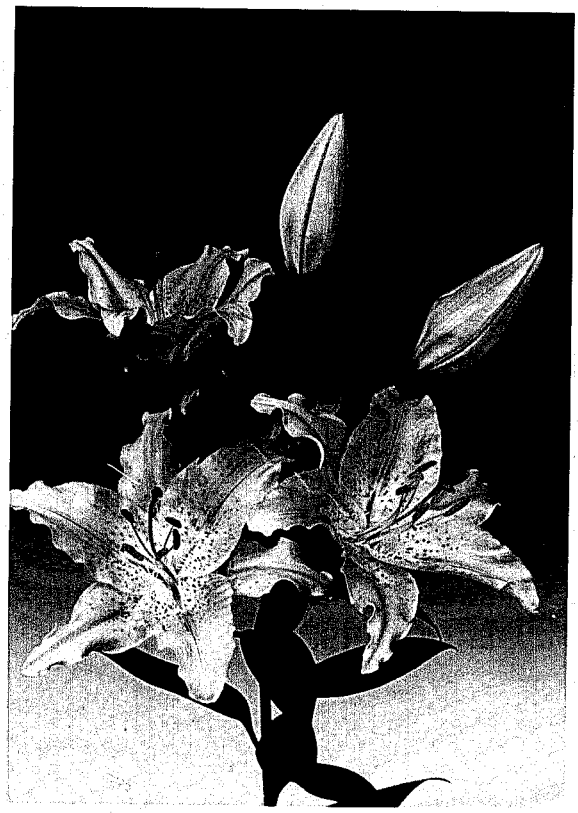

* * * * *